US010602930B2

(12) United States Patent
Lawrence et al.

(10) Patent No.: US 10,602,930 B2
(45) Date of Patent: Mar. 31, 2020

(54) MULTI-BIOMETRIC-FACTOR, INTERNET OF THINGS (IOT), SECURED NETWORK

(71) Applicant: Bank of America Corporation, Charlotte, NC (US)

(72) Inventors: Patrick Nicholas Lawrence, Plano, TX (US); Jesse Strickland Newsom, III, Charlotte, NC (US); Victoria Lynn Dravneek, Charlotte, NC (US); John Christopher Checco, Stony Point, NY (US); Hitesh J. Shah, Seattle, WA (US)

(73) Assignee: Bank of America Corporation, Charlotte, NC (US)

( * ) Notice: Subject to any disclaimer, the term of this patent is extended or adjusted under 35 U.S.C. 154(b) by 252 days.

(21) Appl. No.: 15/939,642

(22) Filed: Mar. 29, 2018

(65) Prior Publication Data
US 2019/0298173 A1 Oct. 3, 2019

(51) Int. Cl.
*H04L 29/06* (2006.01)
*A61B 5/00* (2006.01)
(Continued)

(52) U.S. Cl.
CPC .......... *A61B 5/0024* (2013.01); *A61B 5/0022* (2013.01); *A61B 5/01* (2013.01);
(Continued)

(58) Field of Classification Search
None
See application file for complete search history.

(56) References Cited

U.S. PATENT DOCUMENTS 9,319,404 B2 4/2016 Svigals
9,485,231 B1 11/2016 Reese
(Continued)

OTHER PUBLICATIONS

Bhatt, Smriti et al. An Access Control Framework for Cloud-Enabled Wearable Internet of Things. 2017 IEEE 3rd International Conference on Collaboration and Internet Computing (CIC). https://ieeexplore.ieee.org/stamp/stamp.jsp?tp=&arnumber=8181511 (Year: 2017).*

(Continued)

*Primary Examiner* — Jeremiah L Avery
(74) *Attorney, Agent, or Firm* — Weiss & Arons LLP; Michael A. Springs, Esq.

(57) ABSTRACT

A method for authenticating to a network comprising a plurality of Internet of Things ("IoT") devices is provided. The method may include using a mobile telephone apparatus, a wrist-worn apparatus and a head-worn apparatus to monitor the level of at least one of a wearer's pulse, body temperature, voice, gait and/or other biorhythmic indicator. One of the aforementioned apparatus may operate as a hub apparatus. The method may further include using the hub apparatus to assign a federated biometric marker based at least in part on the first, second and third biometric markers. The method may also include using artificial intelligence to monitor for one or more outliers with respect to historical monitoring. Each of the one or more outliers may include a magnitude that exceeds a security threshold difference between the current magnitude and the historically monitored magnitude. When the difference in magnitude exceeds a security threshold difference between the current magnitude and the historically monitored magnitude the method may quarantine apparatus associated with the outlier.

23 Claims, 7 Drawing Sheets

(51) Int. Cl.
  *G06F 21/50* (2013.01)
  *A61B 5/01* (2006.01)
  *A61B 5/024* (2006.01)
  *H04L 29/08* (2006.01)
  *A61B 5/11* (2006.01)

(52) U.S. Cl.
  CPC .............. *A61B 5/024* (2013.01); *A61B 5/112* (2013.01); *A61B 5/6814* (2013.01); *A61B 5/6824* (2013.01); *G06F 21/50* (2013.01); *H04L 67/12* (2013.01)

(56) References Cited

U.S. PATENT DOCUMENTS

| | | | |
|---|---|---|---|
| 9,538,311 | B2 | 1/2017 | Baum et al. |
| 9,565,192 | B2 | 2/2017 | Chillappa et al. |
| 9,591,016 | B1 | 3/2017 | Palmieri et al. |
| 9,699,659 | B2 | 7/2017 | Zehavi et al. |
| 9,699,814 | B2 | 7/2017 | Zakaria et al. |
| 9,716,595 | B1 | 7/2017 | Kravitz et al. |
| 9,729,528 | B2 | 8/2017 | Zakaria et al. |
| 9,825,921 | B2 | 11/2017 | Reese |
| 9,832,026 | B2 | 11/2017 | Kravitz et al. |
| 9,875,510 | B1 | 1/2018 | Kasper |
| 10,251,053 | B1 | 4/2019 | Paczkowski |
| 10,303,869 | B1* | 5/2019 | Duke .................. G06F 21/36 |
| 2015/0033305 | A1* | 1/2015 | Shear .................. G06F 21/575 726/6 |
| 2016/0050213 | A1* | 2/2016 | Storr .................. G06F 21/32 726/6 |
| 2016/0173495 | A1 | 6/2016 | Joo |
| 2016/0248746 | A1 | 8/2016 | James et al. |
| 2016/0259937 | A1 | 9/2016 | Ford et al. |
| 2016/0260095 | A1 | 9/2016 | Ford |
| 2016/0337127 | A1 | 11/2016 | Schultz et al. |
| 2016/0366181 | A1 | 12/2016 | Smith et al. |
| 2017/0063566 | A1* | 3/2017 | Seminario .......... H04L 12/2816 |
| 2017/0091548 | A1* | 3/2017 | Agrawal ............ G06K 9/00604 |
| 2017/0140141 | A1* | 5/2017 | Yan ..................... G06F 21/316 |
| 2017/0143267 | A1* | 5/2017 | Kovacs ................ A61B 5/6887 |
| 2017/0163444 | A1 | 6/2017 | McLaughlin et al. |
| 2017/0289184 | A1 | 10/2017 | C et al. |
| 2017/0346817 | A1* | 11/2017 | Gordon .............. G02B 27/0172 |
| 2018/0039990 | A1* | 2/2018 | Lindemann ............ G06F 21/31 |
| 2018/0253451 | A1 | 9/2018 | Callan et al. |
| 2019/0172566 | A1 | 6/2019 | Schulman et al. |
| 2019/0289454 | A1 | 9/2019 | Inoue |
| 2019/0349190 | A1 | 11/2019 | Smith et al. |

OTHER PUBLICATIONS

Lu, Duo et al. Multifactor User Authentication with In-Air-Handwriting and Hand Geometry. 2018 International Conference on Biometrics (ICB). https://ieeexplore.ieee.org/stamp/stamp.jsp?tp=&arnumber=8411230 (Year: 2018).*

Kurkovsky, Stan et al. RFID-Enabled Authentication: Privacy Implications. IEEE Technology and Society Magazine, vol. 30, Issue: 3. https://ieeexplore.ieee.org/stamp/stamp.jsp?tp=&arnumber=6017257 (Year: 2011).*

"Securing the Internet of Things: A Proposed Framework," https://www.cisco.com/c/en/us/about/security-center/secure-iot-proposed-framework.html, Mar. 16, 2016.

"Global Hacker Botnet tops 6 million hijacked devices," http://www.computerweekly.com/news/450427023/Global-hacker-botnet-tops-6-million-hijacked-devices, Sep. 27, 2017.

* cited by examiner

MULTI-BIOMETRIC-FACTOR, INTERNET OF THINGS (IOT), SECURED NETWORK

FIELD OF TECHNOLOGY

Aspects of the invention relate to network security. More specifically, aspects of the invention relate to securing Internet of Things (IoT) device networks using biometric, multifactor security measures.

BACKGROUND OF THE DISCLOSURE

Multi-biometric-factor security measures are well known. These security measures are used in many different fields of science and industry.

However, many uses of multi-biometric-factor security measures fail to include systems and/or methods for resolving conflicts in systems that involve multi-biometric-factor security measures. Furthermore, many uses of multi-biometric-factor security measures fail to include systems and/or methods for analyzing the effects of conflicts in systems that involve multi-biometric-factor security measures. Yet fewer systems using multi-biometric-factor security measures fail to provide systems and/or methods for resolving conflicts in systems that involve multi-biometric-factor security measures. It would yet further desirable to provide systems and/or methods for mitigating the effects of conflicts in IoT device network systems that involve multi-biometric-factor security measures.

It is an objective of the present embodiments to provide systems and methods for providing biometric, multifactor security measures for use with an IoT device network.

It is a further objective of the present embodiments to provide systems and/or methods for analyzing the effects of conflicts in IoT device network systems that involve multi-biometric-factor security measures.

It is a still further objective of the present embodiments to provide systems and/or methods for resolving conflicts in IoT device network systems that involve multi-biometric-factor security measures.

It is a yet further objective of the present embodiments to provide systems and/or methods for mitigating the effects of conflicts in IoT device network systems that involve multi-biometric-factor security measures.

SUMMARY OF THE DISCLOSURE

Methods and apparatus for verifying an individual using the various IoT devices that are worn by the individual are provided.

In some embodiments, the methods and apparatus may relate to an Automated Teller Machine ("ATM"). In such embodiments, an ATM can recognize that a customer is wearing six devices. Upon receipt of a biometrics multifactor authentication in addition to the determination of the wearable devices, the ATM can determine that the customer is who he says he is.

In certain embodiments, natural language processing can be used to identify voice, and/or a digital signature associated with voice, as part of another level of the authentication process. In certain instances, multiple disparate levels of authentication increase assurance in the authentication process.

One further aspect that combines the foregoing embodiments may involve the following feature. In order to make the system more resilient to failures occurring within component system parts, the system may monitor the individual devices for overall device health such as power level, etc. Then, upon detection of an overall device health alert condition, such as a lower power condition, the system could appropriately weight the contribution of the low power device to the authentication determination.

For example, if someone's electronic fitness watch exhibits a low battery level, the system may preferably send a signal regarding the low battery level to an ATM. The ATM could then respond to the signal by selecting an authentication path that omits, or reduces the importance of the contribution of, the electronic fitness watch. Then the ATM could preferably authenticate based substantially on the input from voice information retrieved from a tablet device and from gait information from a mobile phone device. In this way, the ATM user and the ATM operator could preferably both benefit from the system flexibility in authenticating a transaction that was not fraudulent, but, because of technical difficulties, may exhibit behavior that appears to be fraudulent.

Moreover, artificial intelligence ("AI") can be included to provide anomaly and/or outlier detection. AI can be used to develop signatures. The signatures can be compared with known factors affecting biometric markers and/or historical performance of biometric markers. In certain embodiments, a central AI system can monitor for outliers. Significant compression of information can be used by transmitting categories instead of raw data.

When it is determined that a device, or a device system, has been compromised, the procedure may include:
1. determining whether the system is critical for a particular scenario;
2. shutting down a non-critical system or performing a staged shutdown of a critical system; and/or
3. if a compromised system is shut down, determining a security confidence level at a point in time following the shutdown. If the confidence level is sufficiently high to continue operation, then continue operation. If the confidence level is not sufficiently high to continue operation, halt operation unless there is some other overriding concern, such as, for example, an immediate threat to life.

In a somewhat-related embodiment, another feature relates to increasing the assurance level associated with authenticating high-assurance applications. In this case, an emergency, high-assurance, protocol may require more immediate, and more difficult to spoof, responses. As such, a higher level of authentication can operate in the face of some error by checking down to additional forms of biometric authentication without having to lock someone out.

In certain exemplary networks, each IoT device may include its own AI. Some embodiments may link the AI of each device together, either by providing a link or leveraging the linking mechanisms and communications protocols available in each device, in order to create a linked AI system. In some embodiments, a user can authenticate himself over the normal course of operation of the network using a combination of devices to authenticate.

As part of certain embodiments, systems and/or methods may identify an immediate threat to life for the various systems inside a human body. In these or other embodiments, if one of the IoT devices receives a user's pulse, then the system may access cardiac, or cardiac device irregularities and may be able to respond to or communicate regarding same. For example if a device detects a pacemaker irregularity or detects that the battery of the pacemaker goes low, it may communicate a trigger to an emergency system (911) or perform some other suitable remedial or alarm action.

Some embodiments may also leverage the biometric markers to determine risk with regards to insurance. For example, such data may used to formulate and/or adjust actuarial data for use in providing capital for loans, underwriting auto insurance, underwriting life insurance, etc.

This data could also be leveraged to determine likelihood for purchasing products and services. For example, biometric markers can indicate life stage and life style. If the person's data indicates they travel a certain pre-determined distance to work each day, a company could provide instruction to the person to move to a closer location and, pursuant thereto, provide amenable terms on a loan. Similarly, if the data indicates activity has reduced over time, one could suggest a personal trainer that is in the vicinity of the person with an easy payment method via a suitable method processing system.

A federated identifier may be based on information retrieved using an individual's wearable IoT devices. The identifier may include separate and individual information relating to at least one of a wearer's pulse, body temperature, voice, gait and/or other suitable biorhythmic indicator. The wearable IoT devices may confirm that a watch or other suitable wearable IoT device is being worn by the correct person based on his or her biorhythmic manner.

In some embodiments, the federated identifier may be connected to an appliance's network, such as to determine when milk is out, or past its due date. In other embodiments, the appliances may monitor the odors in a refrigerator to determine whether some food is no longer sanitary, or has become rotten.

The federated identifier can authenticate a person in real time using Bluetooth, low power, Beacon, etc.

In certain embodiments, the federated identifier can be used to speed up a mortgage process. In these embodiments, a trusted financial institution (FI) can act as the validator of the federated identifier. For example, each of the biometric markers can be transmitted for validation to the FI. The FI stores historical values for the biometric markers and, in response to receipt of current biometric markers, can validate the identity of the user and speed a mortgage process or other suitable financial process.

A secure IoT network according to certain embodiments, may leverage devices in order to speed up a real estate transaction process as follows. For example, each contributor in the real estate process may be equipped with a hardware token(s) and the contributors can communicate with each other via the token. This improved process can reduce the 45-60 day mortgage process to 7 days.

In certain embodiments, a federated identifier generated by a secure IoT network can server as a platform trigger. For example, the federated identifier can be used to authenticate, unlock, and/or set the internal settings of, a car. In some embodiments, the identifier can run in transaction mode. The identifier can be used to register devices as a part of a transaction component. It should be appreciated that customer consent should preferably be required at each transaction to minimize unwanted, or unauthorized, connections.

Biometric information, retrieved as information corresponding to one or more biometric markers, should preferably be combined with possession of the IoT devices in order to secure the communication with the devices. Such biometric information may include pace of steps, referred to commonly as gait. A historic review of any predetermined biometric behavior may be used to build a baseline of biometric behavior.

Upon determination that a device may be in another's possession, an ATM or other financial service may question a user for an under duress code, perform a picture match, or other suitable security evaluation to enable an override of in-place security systems.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE DISCLOSURE

Figure 1:
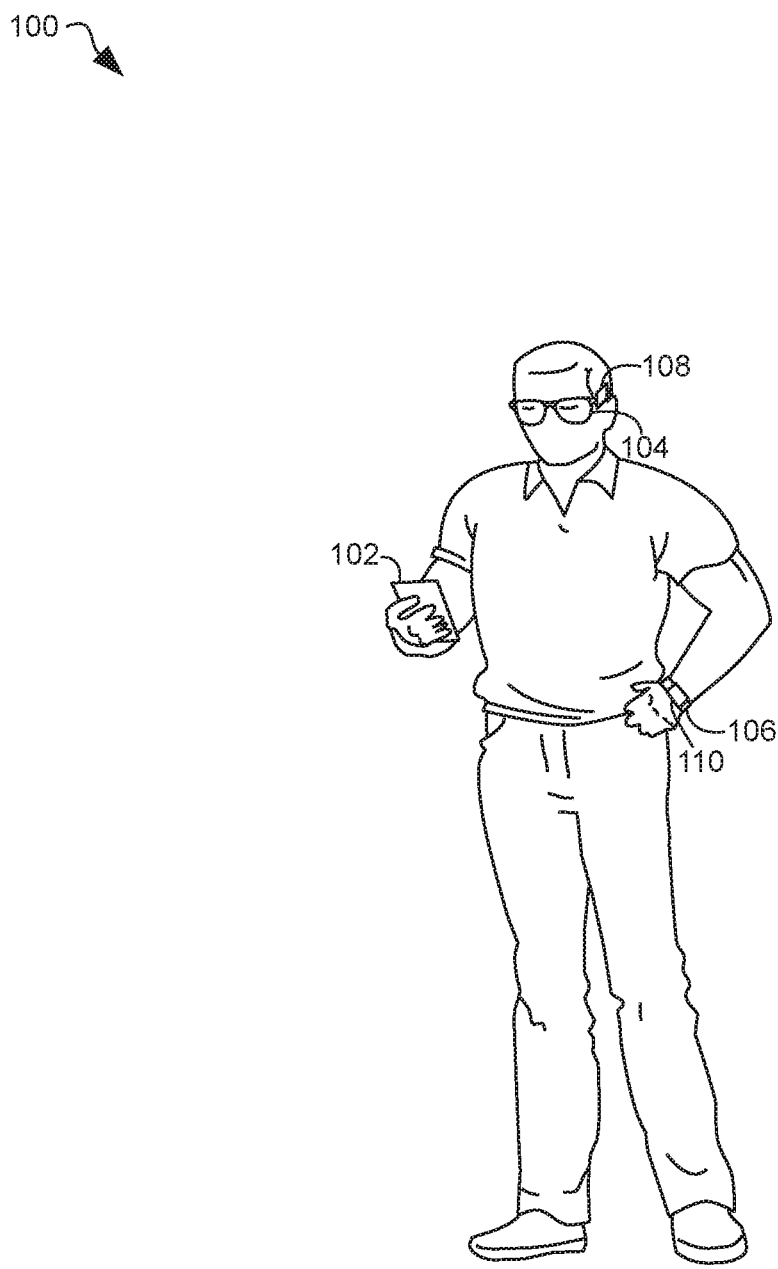
FIG. 1 shows a system according to certain embodiments with three exemplary user-worn electronic devices or apparatuses.

A method for authenticated to a network where the network includes multiple Internet of Things (IoT) devices is provided. The method may include using a mobile telephone apparatus to monitor a first biometric marker. The first biometric marker may indicate the level of at least one of a wearer's pulse, body temperature, voice, gait and/or other biorhythmic indicator.

The method may include using an electronic wrist-worn apparatus to monitor a second biometric marker. The second biometric marker may indicate the level of at least one of a wearer's pulse, body temperature, voice, gait and/or other biorhythmic indicator.

The method may also include using an electronic head-worn apparatus to monitor a third biometric marker. The third biometric marker may indicate the level of at least one of a wearer's pulse, body temperature, voice, gait and/or other biorhythmic indicator.

In some embodiments, one of the mobile telephone apparatus, the electronic wrist-worn apparatus, and the electronic head-worn apparatus may operate as a hub apparatus. The mobile telephone apparatus may be configured to transmit the first biometric marker to the hub apparatus, the electronic wrist-worn apparatus may be configured to transmit the second biometric marker to the hub apparatus and the electronic head-worn apparatus may be configured to transmit the third biometric marker to the hub apparatus.

The hub apparatus may assign a federated biometric marker based at least in part on the first, second and third biometric markers. The federated biometric marker may preferably presenting a multifactor authorization signal. The multifactor authorization signal may be used to compare a measured level of at least one of a wearer's pulse, body temperature, voice, gait and/or other biorhythmic indicator from the first biometric marker with a measured level of at least one of a wearer's pulse, body temperature, voice, gait and/or other biorhythmic indicator from the second biometric marker. When the comparison reveals that at least one of a wearer's pulse, body temperature, voice, gait and/or other biorhythmic indicator from the first biometric marker fails to match a measured level of at least one of a wearer's pulse, body temperature, voice, gait and/or other biorhythmic indicator from the second biometric marker, then the method may determine whether the failure to match exceeds a security threshold.

When a magnitude of a value assigned to the failure to match exceeds a security threshold, the method may further include comparing each of the measured levels of the non-matched item of the mobile telephone apparatus and the wrist-worn apparatus to a measured level of the non-matched item as measured by the electronic-head worn apparatus. When one of the measured levels of the non-matched item is matched by the electronic-head worn apparatus then the method may include quarantining the one of the mobile telephone apparatus and the electronic wrist-worn apparatus that measured the non-matched item.

In certain embodiments, the first biometric marker may be restricted to one of the of wearer's pulse, body temperature, voice, gait and/or other biorhythmic indicator.

In certain embodiments, the second biometric marker may be restricted to one of the of wearer's pulse, body temperature, voice, gait and/or other biorhythmic indicator.

In certain embodiments, the third biometric marker may be restricted to one of the of wearer's pulse, body temperature, voice, gait and/or other biorhythmic indicator.

When any one of the first biometric marker, the second biometric marker and the third biometric marker indicates a voice signature of a user, the voice signature being obtained using natural language processing.

Certain embodiments may involve using artificial intelligence to monitor at least one of the first biometric marker, the second biometric marker and the third biometric marker for one or more outliers. A marker may be determined as an outlier when it is compared to values derived from historical monitoring of at least one of the first biometric marker, the second biometric marker and the third biometric marker. Each of the one or more outliers may include a value that includes a magnitude that exceeds a security threshold difference between the current magnitude and the historically monitored magnitude.

The method may also include performing renewed monitoring of the first, second and third biometric markers following the shutting down the non-critical aspect. Based on the renewed monitoring, for the one or more outliers, the method may determine whether a difference in a value associated with the one or more outliers from prior to the shutting down to after the shutting down was recognized. When a pre-determined change in a value was recognized, the method may further shut down the device associated with the one or more outliers.

Quarantining may preferably include determining whether ramifications associated with the non-matched item relate to a life-threatening scenario. If the ramifications associated with the non-matched item do not relate to a life-threatening scenario, then the method may shut down a non-critical aspect of the one of the mobile telephone apparatus and the electronic wrist-worn apparatus that measured the non-matched item. It should be noted, however, that quarantining may include any suitable process for restricting communication, or other limitation of communication, between the apparatus that detected the non-matched item and the remainder of the network.

Certain embodiments may include a multi-biometric-factor, internet of things ("IoT"), secured network system. The network may include a plurality of Internet of Things IoT devices. The devices may include a first electronic, body-worn apparatus for monitoring a first biometric marker, said first biometric marker indicating the level of at least one of a wearer's pulse, body temperature, voice, gait and/or other biorhythmic indicator; a second electronic, body-worn, apparatus to monitor a second biometric marker, said second biometric marker indicating the level of at least one of a wearer's pulse, body temperature, voice, gait and/or other biorhythmic indicator, and a third electronic body-worn apparatus to monitor a third biometric marker, said third biometric marker indicating the level of at least one of a wearer's pulse, body temperature, voice, gait and/or other biorhythmic indicator.

In such a system, the hub apparatus may be configured to assign a federated biometric marker based at least in part on the first, second and third biometric markers. When a failure to match between a marker detected on two apparatuses exceeds a security threshold, then the hub compares the measured levels of the non-matched item of the first body-worn apparatus and the second body-worn apparatus to a level as measured by the third body-worn apparatus. When one of the measured levels of the non-matched item of the first body-worn apparatus and the second body-worn apparatus is matched by the third body-worn apparatus then the system may be configured to quarantine a non-matching one of the first body-worn apparatus and the second body-worn apparatus.

Apparatus and methods described herein are illustrative. Apparatus and methods in accordance with this disclosure will now be described in connection with the figures, which form a part hereof. The figures show illustrative features of apparatus and method steps in accordance with the principles of this disclosure. It is to be understood that other embodiments may be utilized and that structural, functional and procedural modifications may be made without departing from the scope and spirit of the present disclosure.

The steps of methods may be performed in an order other than the order shown or described herein. Embodiments may omit steps shown or described in connection with illustrative methods. Embodiments may include steps that are neither shown nor described in connection with illustrative methods.

Illustrative method steps may be combined. For example, an illustrative method may include steps shown in connection with another illustrative method.

Apparatus may omit features shown or described in connection with illustrative apparatus. Embodiments may include features that are neither shown nor described in connection with the illustrative apparatus. Features of illustrative apparatus may be combined. For example, an illustrative embodiment may include features shown in connection with another illustrative embodiment.

Figure 6:
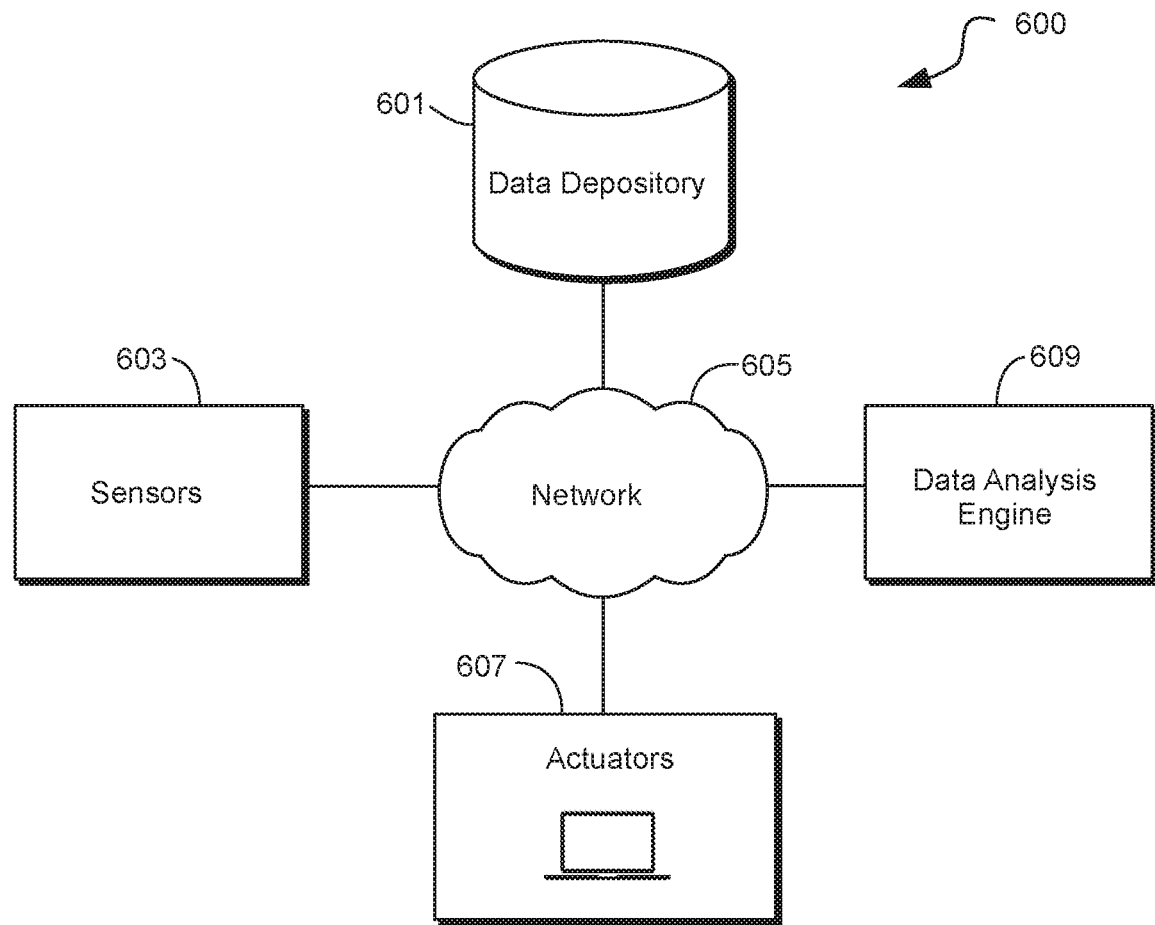
FIG. 6 shows an embodiment of an illustrative system architecture.

FIG. 6 shows illustrative system architecture 600. Architecture 600 may represent an internet of things ("IoT"). The foregoing multi-biometric-factor disclosure, when used in conjunction with IoT devices, may increase security associated with an IoT user-network formed from the devices.

A relevant differentiator between IoT networks and conventional networks is a traffic profile. In an IoT, nodes may not have defined or known network positions, communication protocols or security services. Solutions that allow architecture 600 to function seamlessly and leverage such disparate components are disclosed herein.

Architecture 600 may include nodes. Each node may represent an IoT device for which providence is known. Each node may include two or more nodes. FIG. 6 shows exemplary nodes 601, 603, 605, 607 and 609. The architecture includes sensors 603. Sensors 603 may include devices that detect changes in a physical or virtual environment. For example sensors may measure audio, rainfall, temperature or water levels. Sensors may measure electronic network traffic, electronic signals (e.g., input or output) or frequency of user logins from within a predefined geographic area. With respect to the current multi-biometric-factor disclosure, nodes may measure biometric indicators such as pulse, body temperature, voice, gait and/or other biorhythmic indicator.

Sensors may be any suitable size. For example, sensors may be a few millimeters in size. Sensors may be deployed in a wide variety of locations. For example, sensors may be deployed in military battlefields, industrial plants, in orchards, in clothing, automobiles, smart phones, jewelry or refrigerators. Sensors may be relatively inexpensive and have low energy consumption. Sensors may "sense" two or more stimuli or environmental changes.

Captured data may be transmitted using any suitable transmission method. For example, data captured by a sensor may be extracted by a mobile phone. Sensors may leverage a communication link provided by a mobile phone to communicate captured data to another node. Sensors may leverage an independent communication link to communicate with another node and/or a network hub.

Each sensor may be a node and each sensor may be assigned a unique identifier (ID). For example, sensors may be identified by one or more radio frequency identification ("RFID") tags. The RFID tag may be stimulated to transmit identity information about the sensor or any other information stored on the RFID tag.

Captured data may be transmitted by the sensor and processed far from the location of the sensor that captured the data. For example, captured data may be transmitted from one node to another node until the captured data reaches data repository 601.

Sensors may be positioned and capture data from diverse locations. Locations may include geographic locations or virtual locations on electronic networks. Captured data may be transmitted to a location where information is needed for decisioning or consumption, which may not be the same place the data was captured or generated. Data synchronization protocols and caching techniques may be deployed to ensure availability of information at, or delivery to, a desired node. For example, a location where data is captured may not have continuous reliable network connectivity. Accordingly, captured data may be stored locally on the sensor for an amount of time prior to transmission or broadcast to another node.

Contextually, captured data may provide information not only about the physical environment surrounding a sensor, but the capturing of data from multiple sensors may provide data that signifies an event. Sensors may be grouped. Sensors may be grouped based on physical proximity or based on the content (or expected content) of data captured. Sensors may be grouped virtually. Other nodes, such as data analysis engine 109 may create and/or be included in such groups. In some embodiments, the captured data may be organized by data repository 601.

Based on data captured from sensors 603, actuators 607 may respond to a detected event. Based on the capture and analysis of multiple sources of data, actuators 607 may be instructed to take action without human intervention.

Generally, sensors and other nodes that form part of architecture 600 may include a processor circuit. The processor circuit may control overall operation of a node and its associated components. A processor circuit may include hardware, such as one or more integrated circuits that form a chipset. The hardware may include digital or analog logic circuitry configured to perform any suitable operation.

A processor circuit may include one or more of the following components: I/O circuitry, which may include a transmitter device and a receiver device and may interface with fiber optic cable, coaxial cable, telephone lines, wireless devices, PHY layer hardware, a keypad/display control device or any other suitable encoded media or devices; peripheral devices, which may include counter timers, real-time timers, power-on reset generators or any other suitable peripheral devices; a logical processing device, which may compute data structural information, structural parameters of the data, quantify indices; and machine-readable memory.

Machine-readable memory may be configured to store, in machine-readable data structures: captured data, electronic signatures of biometric features or any other suitable information or data structures. Components of a processor circuit may be coupled together by a system bus, wirelessly or by other interconnections and may be present on one or more circuit boards. In some embodiments, the components may be integrated into a single chip. The chip may be silicon-based.

The node may include RAM, ROM, an input/output ("I/O") module and a non-transitory or non-volatile memory. The I/O module may include a microphone, button and/or touch screen which may accept user-provided input. The I/O module may include one or more of a speaker for providing audio output and a video display for providing textual, audiovisual and/or graphical output.

Software applications may be stored within the non-transitory memory and/or other storage medium. Software applications may provide instructions to the processor for enabling a node to perform various functions. For example, the non-transitory memory may store software applications used by a node, such as an operating system, application programs, and an associated database. Alternatively, some or all of computer executable instructions of a node may be embodied in hardware or firmware components of the node.

Software application programs, which may be used by a node, may include computer executable instructions for invoking user functionality related to communication, such as email, short message service ("SMS"), and voice input and speech recognition applications. Software application programs may utilize one or more algorithms that request alerts, process received executable instructions, perform power management routines or other suitable tasks.

FIG. 1 shows user 100 with three exemplary user-worn electronic devices or apparatuses. These devices include a mobile telephone communications hub device 102, a pair of eyeglasses including a communications module 108 for communication, in certain embodiments with device 102, and a wrist-watch device 106. Wrist-watch device 106 preferably includes a communications module 110 for communication with hub 102.

It should be noted, in some embodiments, each of communications modules 108 and 110 may preferably be used to communicate with hub device 102.

Figure 4:
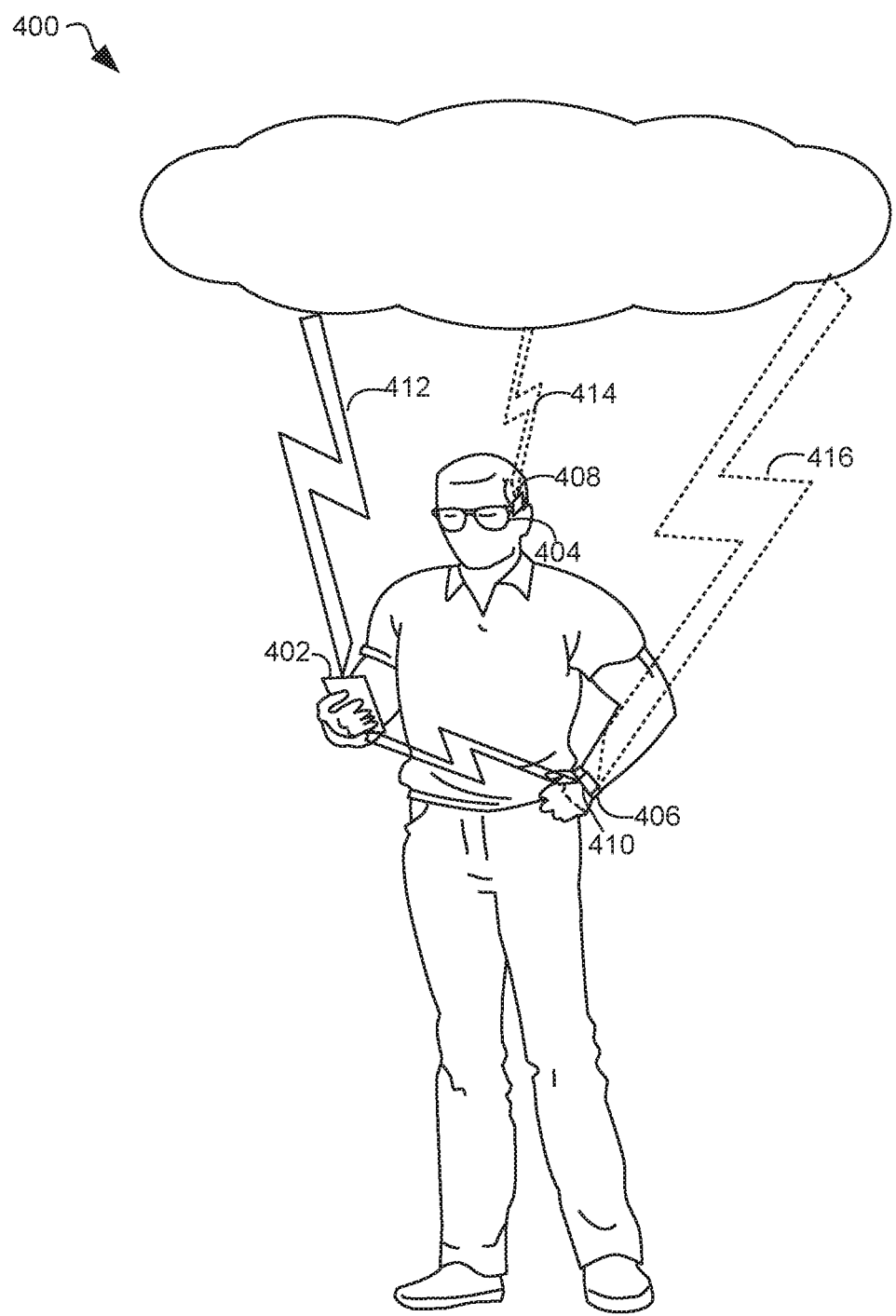
FIG. 4 shows a communication coupling according to certain embodiments.

In other embodiments, each of communications modules 108 and 110 may preferably be used to communicate directly with the internet and/or the cloud via a separate connection. Thereafter, such communications may preferably be rerouted, if necessary, from the internet or the cloud back into the hub for network communications that traverse the internet. FIG. 4 shows the communication coupling to the cloud in detail. Coupling 412, from the hub 402 to cloud 401, is shown as required. Couplings 414 and 416 are shown as optional.

Figure 2:
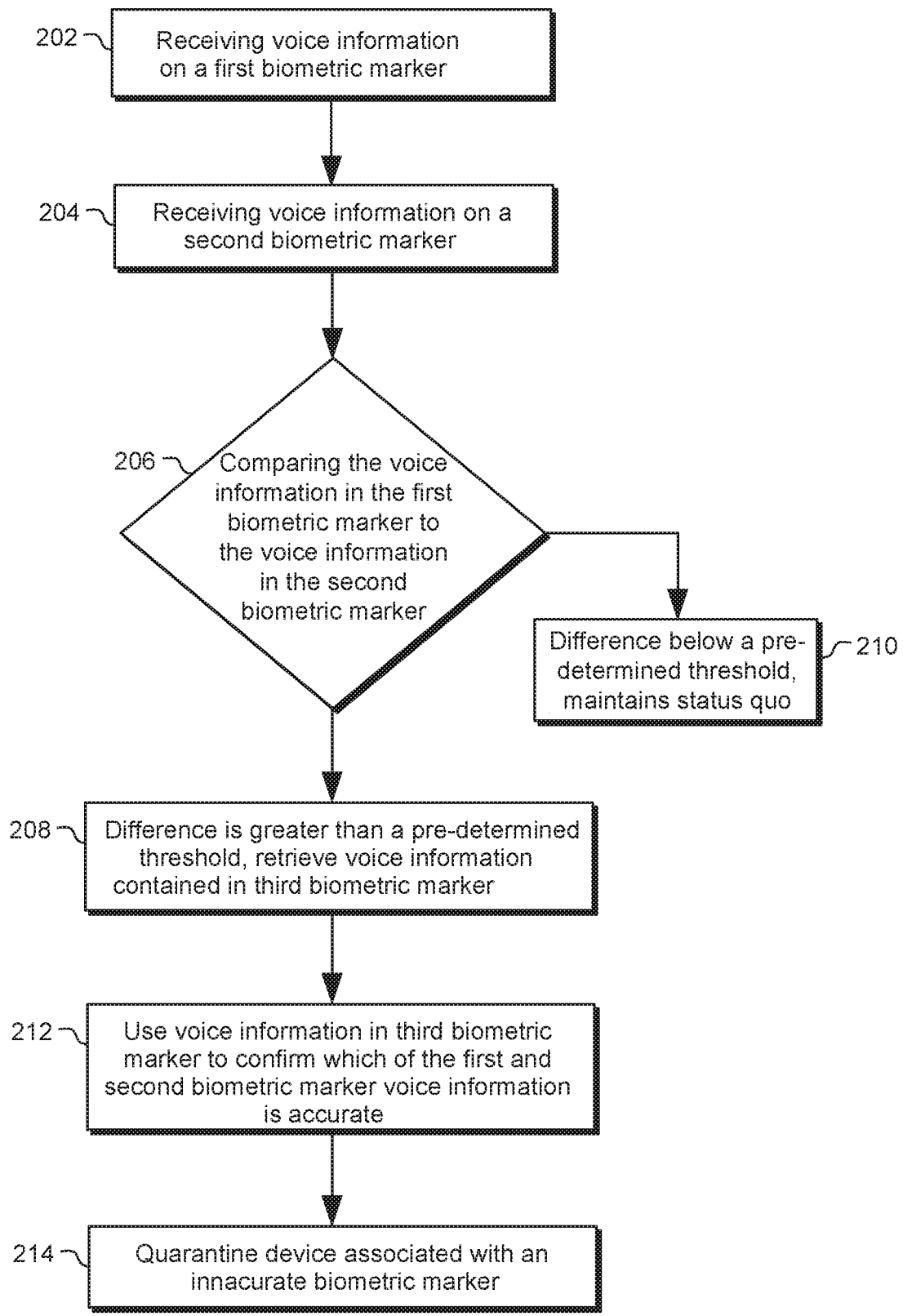
FIG. 2 shows an illustrative flow diagram of an exemplary method according to certain embodiments.

FIG. 2 shows an illustrative flow diagram of an exemplary method according to certain embodiments. Step 202 shows receiving voice information on a first biometric marker. Step 204 shows receiving voice information on a second biometric marker.

Step 206 shows comparing the voice information in the first biometric marker to the voice information in the second biometric marker. Step 210 shows that, if the difference between the voice information in the first biometric marker to the voice information in the second biometric marker is below a pre-determined threshold magnitude, then the system preferably maintains the status quo operation.

Step 208 shows that if the difference is greater than a pre-determined threshold magnitude, then retrieving voice information contained in the third biometric marker. Step 212 shows using the voice information in the third biometric marker to confirm which of the first and second biometric marker voice information is accurate. Step 214 shows quarantining the device associated with the inaccurate biometric marker.

Figure 3:
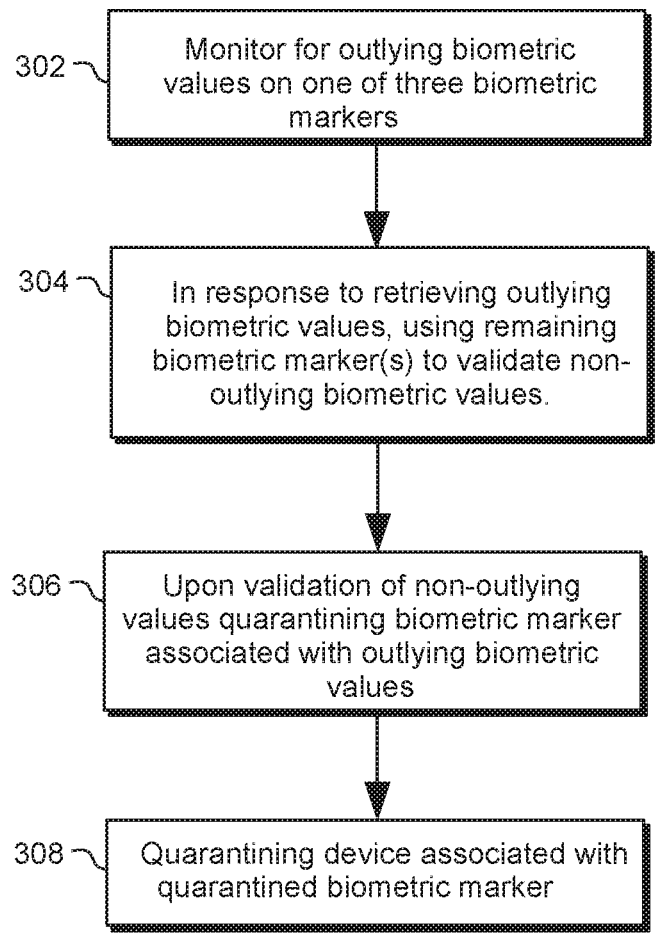
FIG. 3 shows another illustrative flow diagram of an exemplary method according to certain embodiments.

FIG. 3 shows another illustrative flow diagram of an exemplary method according to certain embodiments. Step 302 shows monitoring for outlying biometric values on of the three biometric markers. For the purpose of certain embodiments in this application, an outlying marker may be considered a marker that provides values that are greater, by a pre-determined threshold, than historically measured markers. Alternatively, an outlying marker may be considered a marker that provides information that is different, by a threshold amount, from information regarding the same underlying biometric information as derived by one or more other apparatus.

Step 304 shows, in response to retrieving outlying information biometric values, using remaining biometric marker(s) to validate non-outlying biometric values. Upon validation of non-outlying values, step 306 quarantining biometric marker associated with outlying biometric values. Finally, step 308 shows quarantining the biometric device associated with quarantined biometric marker.

Figure 5:
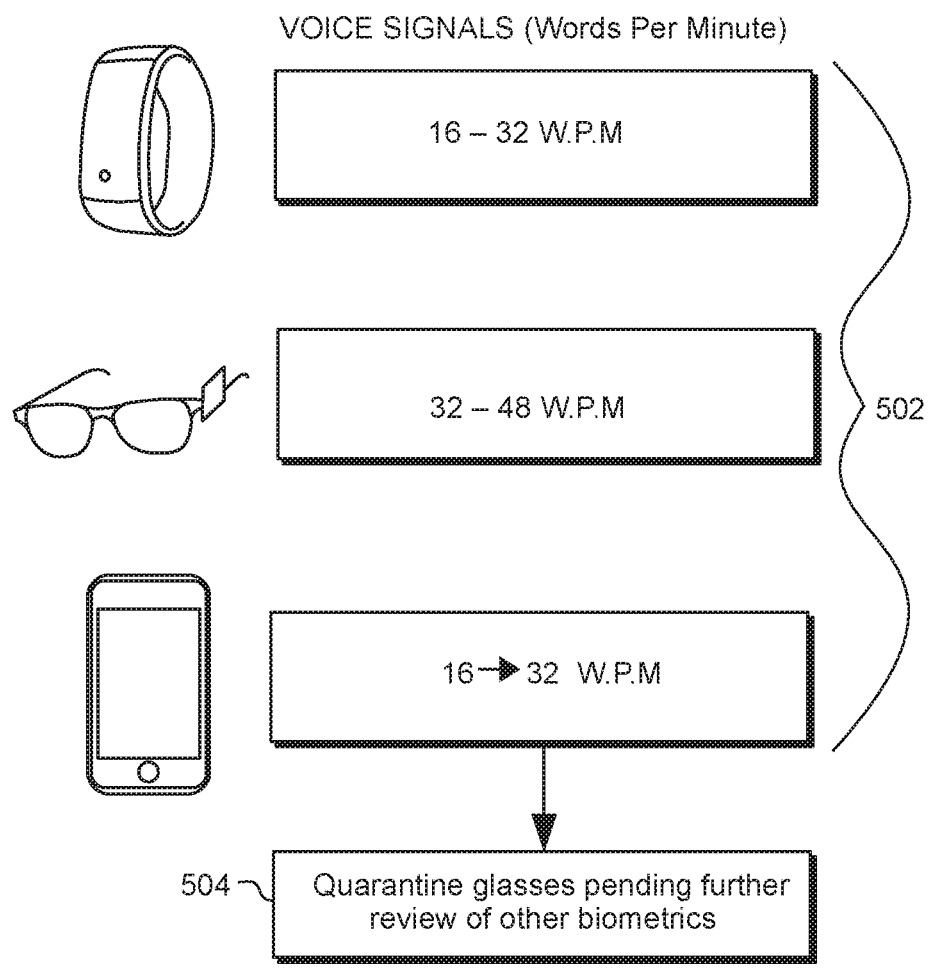
FIG. 5 shows one example of an exemplary determination of an outlying biometric marker according to certain embodiments.

FIG. 5 shows one example of an exemplary determination of an outlying biometric marker. Specifically, FIG. 5 shows determining outlying voice signals. Specifically, at 502, the wrist-watch determines that a person is identified at between 16-32 words per minute (wpm), the eyeglasses determines that a person is identified at between 32-48 words per minute (wpm), and the mobile phone determines that a person is identified at between 16-32 words per minute (wpm). Accordingly, step 504 shows quarantining the glasses pending further review of other biometric signals.

As shown in FIG. 6, a node may operate in a networked environment. A node may be part of two or more networks. A node may support establishing network connections to one or more remote nodes. Such remote nodes may be sensors, actuators or other computing devices. Nodes may be personal computers or servers. Network connections may include a local area network ("LAN") and a wide area network ("WAN"), and may also include other networks. When used in a LAN networking environment, a node may be connected to the LAN through a network interface or adapter. The communication circuit may include the network interface or adapter.

When used in a WAN networking environment, a node may include a modem or other circuitry for establishing communications over a WAN, such as the Internet. The communication circuit may include the modem.

The existence of any of various well-known protocols such as TCP/IP, Ethernet, FTP, HTTP and the like is presumed, and a node can be operated in a client-server configuration to permit a user to retrieve web pages from a web-based server. Web browsers can be used to display and manipulate data on web pages.

Nodes may include various other components, such as a battery, speaker, and antennas. Network nodes may be portable devices such as a laptop, tablet, smartphone, "smart" devices (e.g., watches, eyeglasses, clothing, or other body-worn apparatus having embedded electronic circuitry) or any other suitable device for receiving, storing, transmitting and/or displaying relevant information. Blockchains according to certain embodiments may include providence information for the components and/or for the IoT units themselves.

A node may include a display constructed using organic light emitting diode ("OLED") technology. OLED technology may enhance functionality of a node. OLEDs are typically solid-state semiconductors constructed from a thin film of organic material. OLEDs emit light when electricity is applied across the thin film of organic material. Because OLEDs are constructed using organic materials, OLEDs may be safely disposed without excessive harm to the environment.

Furthermore, OLEDs may be used to construct a display that consumes less power compared to other display technologies. For example, in a Liquid Crystal Display power must be supplied to the entire backlight, even to illuminate just one pixel in the display. In contrast, an OLED display does not necessarily include a backlight. Furthermore, in an OLED display, preferably, only the illuminated pixel draws power.

The power efficiency of OLED technology presents a possibility for designing nodes that provide enhanced security and functionality. Illustrative devices that may be constructed using OLED technology are disclosed in U.S. Pat. No. 9,665,818, which is hereby incorporated by reference herein in its entirety.

A node may be operational with numerous other general purpose or special purpose computing system environments or configurations. Examples of well-known computing systems, environments, and/or configurations that may be suitable for use with the invention include, but are not limited to, personal computers, server computers, handheld or laptop devices, tablets, "smart" devices (e.g., watches, eyeglasses, clothing having embedded electronic circuitry) mobile phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like.

Nodes may utilize computer-executable instructions, such as program modules, being executed by a computer. Generally, program modules include routines, programs, objects, components, data structures, etc. that perform particular tasks or implement particular abstract data types. A node may be operational with distributed computing environments where tasks are performed by remote processing devices that are linked through a communications network. In a distributed computing environment, program modules may be located in both local and remote computer storage media including memory storage devices. Nodes may rely on a network of remote servers hosted on the Internet to store, manage, and process data (e.g., "cloud computing.

Nodes may include a battery. The battery may be a power source for electronic components of the node. For example, the battery may supply power to the display, the communication circuit and the processor circuit. In some embodiments, a node may include a plurality of batteries. Nodes may include solar panels that convert solar energy into electricity that powers one or more components of a node.

Sensors in a single architecture or other grouping may be produced by different manufacturers. Sensors may capture data in different formats. For example, sensors may use different data structures to package captured data. Sensors 603 may utilize different communication protocols to transmit captured data or communicate with other nodes. Despite such operational differences, sensors 603 may operate substantially seamlessly together. Interoperability may allow captured data to be substantially seamlessly captured and interpreted by data analysis engine 609. Based on interpreting the captured data, data analysis engine 609 may issue instructions to actuators 607.

Interoperability may be implemented across any suitable nodes of architecture 600. Interoperability may enable communication between sensors 603 and other nodes. Interoperability may enable architecture 600 to provide services and applications via actuators 607. Interoperability may allow services and content to be provided anywhere, anytime and based on input/output of different nodes.

Data gathering by one or more of sensors 603 may be controlled by one or more other nodes of architecture 600. For example, data analysis engine 609 may control a quantity of data captured by sensors 603. Alternatively, data repository 601 and/or analysis engine 609 may filter or otherwise intelligently process data captured by sensors 603. Interoperability, in view of the data architecture, may also provide for analyzing data and using the data analysis to quarantine one or more of the nodes as set forth herein.

Timing of when data is captured by sensors 603 may be controlled by any suitable node on architecture 600. For example, data may be captured in real-time or at pre-defined intervals such as once a day. Data may also be captured in response to a detected environmental status change.

Data analysis engine 609 may filter data captured by sensors 603. Data analysis engine 603 may repackage or reformat captured data. Data conversion may include transformation of low level raw data (possibly from multiple sensors or groups of sensors) into meaningful information for a target audience or for a target analysis.

For example, captured data intended for human consumption or interaction may be converted into a human understandable format. Captured data intended for machine consumption may be converted into a format readable by a particular machine or node.

Data analysis engine 609 may perform pattern recognition to identify correlations and trends in captured data. Data analysis engine 609 may also evaluate a cost of obtaining data. "Costs" may be monetary (e.g., labor costs or infrastructure costs), time-related or related to a level of intrusion needed to obtain desired data. "Costs" may be bandwidth-related.

For example, a communication link may be associated with a fixed bandwidth. The bandwidth may limit an amount of information or a rate of transmission over the communication link.

For example, a sensor may respond slowly to a request from another node if there is a large amount of informational traffic traveling on a communication link shared with other nodes. The large amount of informational traffic may not leave sufficient bandwidth for the transmitting node to timely communicate with the requesting node.

As a further example, a sensor may respond slowly if the sensor transmits a large amount of captured data. The large amount of information transmitted by the sensor, together with other informational traffic traveling on the shared communication link, may be close to, or exceed the bandwidth of the communication link. As a result, sensors may be unable to transmit captured date in a timely manner.

Data travelling within architecture 600 to/from nodes may be routed along multiple communication links until the transmitted information reaches a desired destination node (e.g., data analysis engine 609). Each communication link may service a number of connected nodes and a respective volume of informational traffic.

It may be difficult to ascertain available bandwidth on a particular communication link. It may be difficult to ascertain which communication links are being utilized to transmit information between nodes. Nodes attempting to transmit information over a communication link may not be aware of a number of connected nodes, a volume of traffic on a particular communication link or a bandwidth capacity of a communication link.

Furthermore, a communication link may be controlled by a different entity from an entity responsible for operation of a particular node. The entity responsible for operation of the node may be unable to monitor a number of nodes that share a communication link, a bandwidth capacity of a communication link or a volume of traffic transmitted on a communication link. Despite difficult to predict conditions on a communication link, it would be desirable for a node to timely respond to a request for information or timely receive desired information.

Sensors 603 may belong to, or operated by, different administrative/management domains. Sensors 603 may be operated by different domains without expressly-defined relationships among such domains. The absence of express relationships enables preferably key-based access to data captured by sensors 603 by one or more architectures having one or more features in common with architecture 600. Groups of sensors may include sensors from two or more administrative domains.

Data repository 601 may receive data captured by sensors 603. In some embodiments, data captured by sensors 603 may be transmitted directly to data analysis engine 609. Data stored in repository 601 may be sorted and analyzed by data analysis engine 609. Data stored in data repository 601 may be so voluminous and complex (e.g., structured/unstructured and/or constantly changing) that traditional data processing application software may be inadequate to meaningfully process the data (e.g., "big data"). Data analysis engine 609 may include software applications specially designed to process large volumes of data ("big data analytics").

Based on captured data, data analysis engine 609 may optimize processes, reduce loss (e.g., fraud), improve customer understanding and targeting, increase automation, decrease latency in products and/or services provided by actuators 607 and identify new analytical models that may utilize data captured by sensors 603.

Architecture 600 may include one or more layers of software applications. Software applications may implement a variety of functions and provide varied services to nodes of architecture 600. Software applications running on data analysis engine 609 may submit requests to sensors 603 for retrieval of specific data to achieve a functional goal provided by actuators 607. Software applications may control data captured by sensors 603 or actions taken by actuators 607. Software applications may control a flow of information within architecture 600.

Software applications may be implemented on a node. A node may be an enterprise system or a "cloud" of computing devices. On device applications may be dependent on a specific hardware configuration. Such hardware requirements may preferably be minimal, such as an extension of the OS/firmware of the device. For example, illustrative software applications for sensors may include TinyOS, Linux, Contiki and RIOT.

Software applications may include middleware. Middleware may connect an operating system or database to other software applications. Middleware may configure and manage hardware such as sensors (e.g., to achieve a target functionality). Middleware may be responsible for aggregating data captured by sensors 603 and passing captured data to data repository 601 and/or data analysis engine 609.

Software applications may provide security services that mitigate threats to the integrity of data captured by sensors 603 or architecture 600 generally.

Actuators 607 may respond to data transmitted or processed by other nodes such as data analysis engine 609. Actuators 607 may include devices that modify the physical state of a physical entity. Actuators 607 may include devices that modify a virtual state of information. For example, actuators 607 may move (translate, rotate, etc.) physical objects or activate/deactivate functionalities of more complex ones. An actuator may dim a light bulb, open a door, change a temperature setting, authorize access to an automated-teller-machine ("ATM") and/or any other suitable functionality. Actuators 607 may verify identities, trigger electronic payments, extend credit or debit accounts.

Within an intelligent networked system such as architecture 600, sensors 603 perform the functions of input devices—they serve as, for example, "eyes," collecting information about their environment. In contrast, actuators 607 act as "hands," implementing decisions based on data captured by sensors 603. A single node may include the functions of sensors and actuators.

Actuators 607 may communicate with data analysis engine 609 and sensors 603. Actuators 607 may include an application programming interface ("API") for communicating with other nodes. Actuators 607 may communicate directly with other nodes using machine-to-machine ("M2M") protocols. Illustrative M2M protocols may include MQ Telemetry Transport ("MQTT"). M2M includes communication between two or more objects without requiring direct human intervention. M2M communications may automate decision-making and communication processes for actuators 607.

In the absence of express relationships between sensors and the devices that access data captured by the sensors, traditional approaches for managing trust, security naming, discovery, or other traditional network services may not be applicable or available. In one particular embodiment, the system disclosed herein for identifying, maintaining and providing information regarding an IoT device, may be used for managing trust and/or resolving discrepancies or other information mismatches of the IoT devices in the network.

Generally, nodes of architecture 600 may interact and cooperate using one or more interaction paradigms. Exemplary interaction paradigms include client-server and peer-to-peer interactions.

As a result of the disparate nature of sensors 603, an architecture, such as architecture 600 incorporating sensors 603 may support a variety of communication protocols.

Illustrative supported protocols may include HyperText Transfer Protocol ("HTTP"), Simple Object Access Protocol ("SOAP"), REpresentational State Transfer ("REST") Constrained Application Protocol ("CoAP"), SensorML, Institute of Electrical and Electronic Engineers ("IEEE") 802.15.4 ("ZigBee") based protocols, IEEE 802.11 based protocols. For example, ZigBee is particularly useful for low-power transmission and requires approximately 20 to 60 mW for 1 mW transmission power over a range of 10 to 100 meters and a data transmission rate of 250 kbit/s.

To further conserve energy, a sensor may communicate wirelessly for short periods of time. Utilizing this approach, one or more standard size single cell cylindrical dry battery batteries (e.g., AA size) may provide requisite computing power and wireless communication for many months.

Communication protocols used by nodes (e.g., sensors or actuators) may not have, or may not be capable of having, security capabilities. A security layer or buffer may be implemented by nodes that receive or rely on data captured by insecure sensors. Sensors or other nodes may be dynamically connected or disconnected from a group or architecture. A security layer or buffer may be modular and quickly scalable meet growth/contraction requirements.

A physical layer may physically link nodes of architecture 600. The physical layer may provide communication pathways or links to move data between multiple sub-networks and nodes. Such communication links may be wired or wireless. Exemplary wireless communication links may include Bluetooth, Wi-Fi, 3G, 4G, 5G and LTE.

Figure 7:
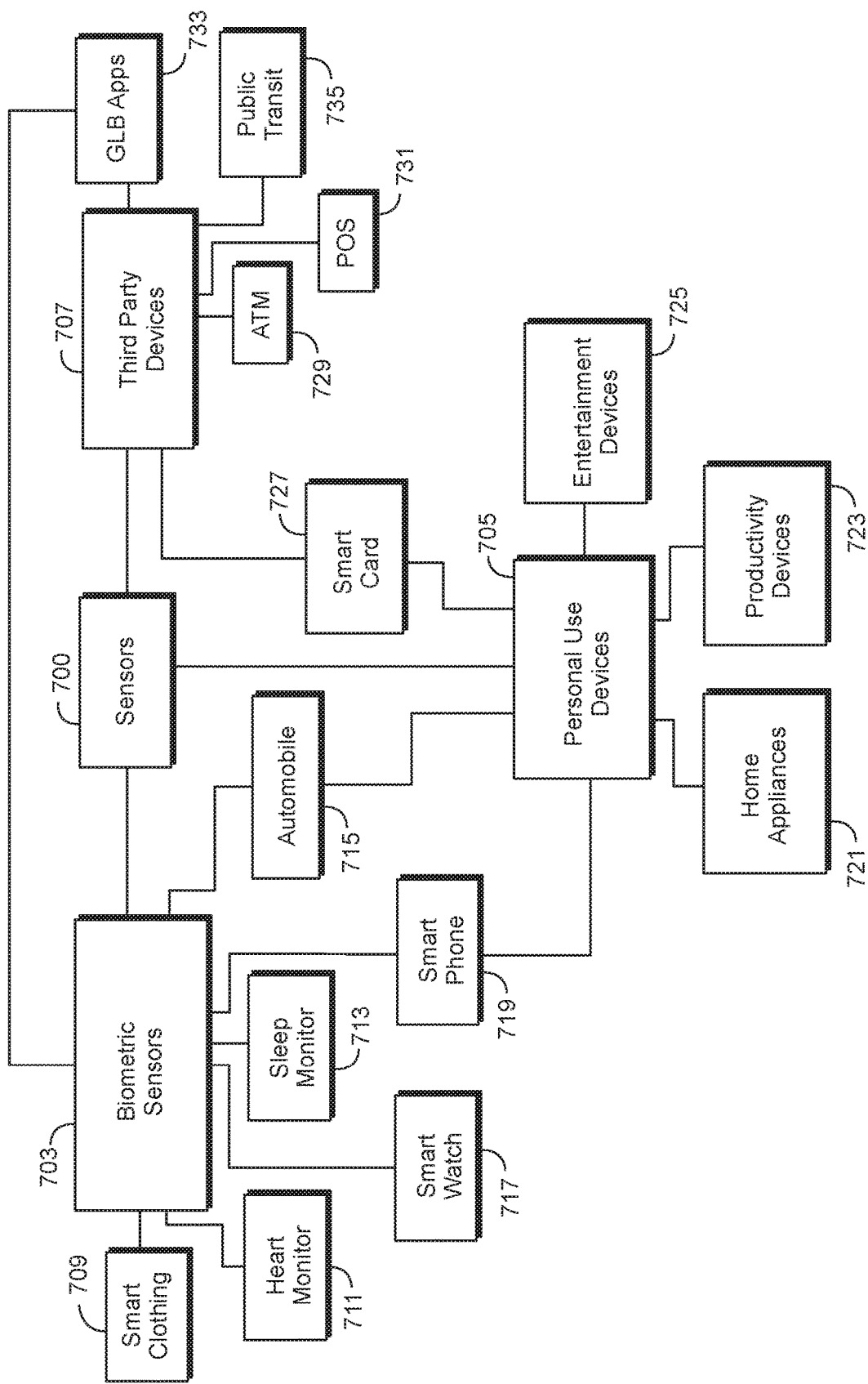
FIG. 7 shows embodiments of illustrative sensors for use with embodiments of the invention.

FIG. 7 shows illustrative sensors 700. Sensors 700 may include or more features of sensors 603 (shown in FIG. 6). Sensors 700 include biometric sensors 703 that sense biometric attributes. For example, biometric sensors may be embedded in IoT devices such as "smart" clothing 709, or other body-worn apparatus, that monitors a wearer's physical condition. Such clothing may capture biometric data, such as pulse rate, temperature, perspiration levels, muscle contraction, heart rhythm and/or physical movement. Smart clothing may be linked to smart phone 719 such as via a Bluetooth® communication link. Smart phone 719 may transmit data captured by smart clothing 709 to one or more other network nodes.

Biometric sensors 703 may include other illustrative sensors such as heart monitor 711, sleep monitor 713, smart watch 719, smart phone 719 and automobile 715.

Sensors 700 may include personal use devices 705. Personal use devices 705 may include sensors embedded in home appliances 721, productivity devices 723 or entertainment devices 725. Productivity devices 723 may include tablets, laptops or other personal computing devices. Entertainment devices may include gaming consoles and the like.

Sensors 700 also include third-party devices 707. Third-party devices may include devices that are not under the direct or exclusive control of a user or whose use is monitored by a third-party. A user may interact with third-party devices 707 to obtain a desired service provided by the third-party.

Exemplary third party devices include smart card 727. Smart card 727 may function as a purchasing instrument. Illustrative purchasing instruments may conform to specifications published by the International Organization for Standardization. Such specifications may include: ISO/IEC 7810, ISO/IEC 7811 and ISO/IEC 7816, which are hereby incorporated herein by reference in their entireties. Suitable purchasing instruments may include a credit card, debit card and other electronic purchasing devices. Such purchasing instruments may sense a location or frequency of use.

Purchasing instruments may include "EMV" chips. EMV is a technology that derives its name from the companies (Europay, MasterCard, and Visa) that helped develop the technology. When the credit card and its associated EMV chip are inserted into a specialized card reader such as point-of-sale terminal ("POS") 731, the reader powers the EMV chip and the EMV chip generates a new authorization code each time the credit card is used. The EMV chip may capture transaction data such as amounts, location or identity of the POS.

Third-party sensors 707 may include ATM 729 and POS 731. ATM 729 and POS 731 may also be actuators. Third-party devices may also include software applications 733. Applications 733 may be used to access services, such as an online banking portal ("OLB"). Such applications may detect biometric features submitted to authorize access to an OLB. Third-party devices may include sensors that capture data associated with power consumption (e.g., smart grids), electronic communication traffic, logistics (package movement) or any other suitable environmental condition.

FIG. 700 shows that sensors may categorically overlap. For example, an application used to access an OLB may capture a biometric feature (e.g., fingerprint) to authenticate a user. Automobile 715 may be in regular communication with a third-party.

Each of the sensors shown in FIG. 700 may include different and possibly incompatible hardware. For example, sensors may each have different operating systems (or none at all), processor types and memory requirements. Sensors 700 may be inexpensive, single-function devices with rudimentary network connectivity. Sensors 700 may be positioned in remote and/or inaccessible locations where human intervention or configuration is difficult.

To conserve power, sensors 700 may utilize 16-bit microcontrollers. Such microcontrollers may use less than 400 µW per MIPS ("million instructions per second") yet may be capable of operating TCP/IPv6 stacks with 4 kB RAM and 24 kB flash memory. As outlined in proposed Internet standard RFC 4944, which is hereby incorporated by reference in its entirety, IPv6 may be implemented over IEEE 802.15.4 (e.g., ZigBee) based wireless communication protocols or other suitable communication protocols.

Furthermore, because of potentially disparate features and characteristics of sensors 700, security solutions disclosed herein may be used to verify an authenticity of a sensor and/or data transmitted by the sensor.

Thus, apparatus and methods for providing multi-biometric-factor, IoT, secured network are provided. Persons skilled in the art will appreciate that the present invention can be practiced by other than the described embodiments, which are presented for purposes of illustration rather than of limitation. The present invention is limited only by the claims that follow.

What is claimed is:

1. A method for authenticating to a network comprising a plurality of Internet of Things (IoT) devices, the method comprising:
    using a mobile telephone apparatus to monitor a first biometric marker, said first biometric marker indicating a level of at least one of a wearer's pulse, body temperature, voice, gait and/or other biorhythmic indicator;
    using an electronic wrist-worn apparatus to monitor a second biometric marker, said second biometric marker indicating the level of at least one of a wearer's pulse, body temperature, voice, gait and/or other biorhythmic indicator;
    using an electronic head-worn apparatus to monitor a third biometric marker, said third biometric marker indicating the level of at least one of a wearer's pulse, body temperature, voice, gait and/or other biorhythmic indicator;
    using one of the mobile telephone apparatus, the electronic wrist-worn apparatus, and the electronic head-worn apparatus to operate as a hub apparatus, wherein:
        the mobile telephone apparatus is configured to transmit the first biometric marker to the hub apparatus;
        the electronic wrist-worn apparatus is configured to transmit the second biometric marker to the hub apparatus; and
        the electronic head-worn apparatus is configured to transmit the third biometric marker to the hub apparatus;
    using the hub apparatus to assign a federated biometric marker based at least in part on the first, second and third biometric markers, said federated biometric marker presenting a multifactor authorization signal;
    using said multifactor authorization signal to compare a measured level of at least one of a wearer's pulse, body temperature, voice, gait and/or other biorhythmic indicator from the first biometric marker with a measured level of at least one of a wearer's pulse, body temperature, voice, gait and/or other biorhythmic indicator from the second biometric marker and, when the comparison reveals that at least one of a wearer's pulse, body temperature, voice, gait and/or other biorhythmic indicator from the first biometric marker fails to match a measured level of at least one of a wearer's pulse, body temperature, voice, gait and/or other biorhythmic indicator from the second biometric marker, then determining whether the failure to match exceeds a security threshold; and
    when a magnitude of a value assigned to the failure to match exceeds a security threshold, comparing each of measured levels of the non-matched item of the mobile telephone apparatus and the wrist-worn apparatus to a measured level of the non-matched item as measured by the electronic head-worn apparatus, and, when one of the measured levels of the non-matched item is matched by the electronic head-worn apparatus then the method may include quarantining the one of the mobile telephone apparatus and the electronic wrist-worn apparatus associated with the measured level the non-matched item.

2. The method of claim 1, wherein the first biometric marker consists of voice.

3. The method of claim 1, wherein the second biometric marker consists wearer's pulse.

4. The method of claim 1, wherein the third biometric marker consists of user's body temperature.

5. The method of claim 1, wherein when any one of the first biometric marker, the second biometric marker and the third biometric marker indicates a voice signature of a user, the voice signature being obtained using natural language processing.

6. The method of claim 1, further comprising using artificial intelligence to monitor at least one of the first biometric marker, the second biometric marker and the third biometric marker for one or more outliers with respect to historical monitoring of at least one of the first biometric marker, the second biometric marker and the third biometric marker, each of said one or more outliers comprising a value that includes a magnitude that exceeds a security threshold difference between a currently-monitored value magnitude and a historically-monitored value magnitude.

7. The method of claim 6 wherein the quarantining further comprises determining whether ramifications associated with the non-matched item relate to a life-threatening scenario and, if the ramifications associated with the non-matched item do not relate to a life-threatening scenario, then shutting down a non-critical aspect of the one of the mobile telephone apparatus and the electronic wrist-worn apparatus that measured the non-matched item.

8. The method of claim 7 further comprising a renewing monitoring of the first, second and third biometric markers following the shutting down the non-critical aspect, and, based on the renewing monitoring, for the one or more outliers, determining whether a pre-determined change in a value associated with the one or more outliers from prior to the shutting down occurred.

9. The method of claim 8 further comprising, when the pre-determined change in a value associated with the one or more outliers from prior to the shutting down occurred shutting down the apparatus associated with the value associated with the one or more outliers.

10. A method for authenticating to network comprising a plurality of Internet of Things ("IoT") devices, the method comprising:
   using a mobile telephone apparatus to monitor a first biometric marker, said first biometric marker indicating a level of at least one of a wearer's pulse, body temperature, voice, gait and/or other biorhythmic indicator;
   using an electronic wrist-worn apparatus to monitor a second biometric marker, said second biometric marker indicating the level of at least one of a wearer's pulse, body temperature, voice, gait and/or other biorhythmic indicator;
   using an electronic head-worn apparatus to monitor a third biometric marker, said third biometric marker indicating the level of at least one of a wearer's pulse, body temperature, voice, gait and/or other biorhythmic indicator;
   using one of the mobile telephone apparatus, the electronic wrist-worn apparatus, and the electronic head-worn apparatus to operate as a hub apparatus, wherein:
      the mobile telephone apparatus is configured to transmit the first biometric marker to the hub apparatus;
      the electronic wrist-worn apparatus is configured to transmit the second biometric marker to the hub apparatus; and
      the electronic head-worn apparatus is configured to transmit the third biometric marker to the hub apparatus;
   using the hub apparatus to assign a federated biometric marker based at least in part on the first, second and third biometric markers, said federated biometric marker presenting a multifactor authorization signal; and
   using artificial intelligence to monitor at least one of the first biometric marker, the second biometric marker and the third biometric marker for one or more outliers with respect to historical monitoring of at least one of the first biometric marker, the second biometric marker and the third biometric marker, each of said one or more outliers comprising a value that includes a magnitude that exceeds a security threshold difference between a current magnitude and a historically monitored magnitude; and, when the value that includes a magnitude exceeds a security threshold difference between the current magnitude and the historically monitored magnitude the method may quarantine the apparatus associated with the outlier.

11. The method of claim 10, wherein the first biometric marker consists of the voice.

12. The method of claim 10, wherein the second biometric marker consists of a wearer's pulse.

13. The method of claim 10, wherein the third biometric marker consists of a user's body temperature.

14. The method of claim 10, wherein when any one of the first biometric marker, the second biometric marker and the third biometric marker indicates a voice signature of a user, the voice signature being obtained using natural language processing.

15. A multi-biometric-factor, internet of things ("IoT"), secured network system, the secured network system comprising a plurality of IoT devices, the secured network system comprising:
   a first electronic, body-worn apparatus for monitoring a first biometric marker, said first biometric marker indicating a level of at least one of a wearer's pulse, body temperature, voice, gait and/or other biorhythmic indicator;
   a second electronic, body-worn, apparatus to monitor a second biometric marker, said second biometric marker indicating the level of at least one of a wearer's pulse, body temperature, voice, gait and/or other biorhythmic indicator;
   a third electronic body-worn apparatus to monitor a third biometric marker, said third biometric marker indicating the level of at least one of a wearer's pulse, body temperature, voice, gait and/or other biorhythmic indicator;
   wherein one of the first, second and third body-worn apparatus is configured to operate as a hub apparatus, and wherein:
      the first electronic body-worn apparatus is configured to transmit the first biometric marker to the hub apparatus;
      the second electronic body-worn apparatus is configured to transmit the second biometric marker to the hub apparatus; and
      the third electronic body-worn apparatus is configured to transmit the third biometric marker to the hub apparatus;
   wherein the hub apparatus is configured to assign a federated biometric marker based at least in part on the first, second and third biometric markers, said federated biometric marker presenting a multifactor authorization signal, said multifactor authorization signal for comparing a measured level of at least one of a wearer's pulse, body temperature, voice, gait and/or other biorhythmic indicator from the first biometric marker with a measured level of at least one of a wearer's pulse, body temperature, voice, gait and/or other biorhythmic indicator from the second biometric marker and, when the comparison reveals that at least one of a wearer's pulse, body temperature, voice, gait and/or other biorhythmic indicator from the first biometric marker fails to match a measured level of at least one of a wearer's pulse, body temperature, voice, gait and/or other biorhythmic indicator from the second biometric marker, then the hub apparatus determines whether the failure to match exceeds a security threshold; and when the failure to match exceeds a security threshold, then the hub apparatus compares the measured level of the non-matched item of the first electronic body-worn apparatus and the second electronic body-worn apparatus to a level as measured by the third electronic body-worn apparatus, and, wherein, when one of the measured levels of the non-matched item of the first electronic body-worn apparatus and the second electronic body-worn apparatus is matched by the third electronic body-worn apparatus, the system is configured to quarantine a non-matching one of the first electronic body-worn apparatus and the second electronic body-worn apparatus.

16. The secured network system of claim 15, wherein the first biometric marker consists of the voice.

17. The secured network system of claim 15, wherein the second biometric marker consists of a wearer's pulse.

18. The secured network system of claim 15, wherein the third biometric marker consists of a user's body temperature.

19. The secured network system of claim 15, wherein when any one of the first biometric marker, the second biometric marker and the third biometric marker indicates a voice signature of a user, the voice signature being obtained using natural language processing.

20. The secured network system of claim 15, further comprising using artificial intelligence to monitor at least one of the first biometric marker, the second biometric marker and the third biometric marker for one or more outliers with respect to historical monitoring of at least one of the first biometric marker, the second biometric marker and the third biometric marker, each of said one or more outliers comprising a value that includes a magnitude that exceeds a security threshold difference between the current magnitude and the historically monitored magnitude.

21. The secured network system of claim 15 wherein the quarantining further comprises determining whether ramifications associated with the non-matched item relate to a life-threatening scenario and, if the ramifications associated with the non-matched item do not relate to a life-threatening scenario, then shutting down a non-critical aspect of the one of the first body-worn apparatus and the second body-worn apparatus that measured the non-matched item.

22. The secured network system of claim 21 further comprising renewing monitoring of the first, second and third biometric markers following the shutting down the non-critical aspect of the one of the first body-worn apparatus and the second body-worn apparatus that measured the non-matched item, and, based on the renewing monitoring, for the one or more outliers, determining whether a pre-determined change in a value associated with the one or more outliers from prior to the shutting down occurred.

23. The secured network system of claim 22 further comprising, when the pre-determined change in a value associated with the one or more outliers from prior to the shutting down occurred shutting down the apparatus associated with the value associated with the one or more outliers.

\* \* \* \* \*